United States Patent
Im et al.

(10) Patent No.: US 10,049,467 B2
(45) Date of Patent: Aug. 14, 2018

(54) APPARATUS AND METHOD FOR RECONSTRUCTING MEDICAL IMAGE

(71) Applicants: VATECH Co., Ltd., Gyeonggi-do (KR); VATECH EWOO Holdings Co., Ltd., Gyeonggi-do (KR)

(72) Inventors: Se Yeol Im, Gyeonggi-do (KR); Tae Woo Kim, Gyeonggi-do (KR); Dong Wan Seo, Gyeonggi-do (KR); Sung Il Choi, Gyeonggi-do (KR); Tae Hee Han, Gyeonggi-do (KR)

(73) Assignees: VATECH Co., Ltd., Gyeonggi-do (KR); VATECH EWOO Holdings Co., Ltd., Gyeonggi-do (KR)

(*) Notice: Subject to any disclaimer, the term of this patent is extended or adjusted under 35 U.S.C. 154(b) by 127 days.

(21) Appl. No.: 15/075,047

(22) Filed: Mar. 18, 2016

(65) Prior Publication Data

US 2016/0275679 A1 Sep. 22, 2016

(30) Foreign Application Priority Data

Mar. 18, 2015 (KR) .................. 10-2015-0037639
Mar. 18, 2015 (KR) .................. 10-2015-0037652
Mar. 18, 2015 (KR) .................. 10-2015-0037657

(51) Int. Cl.
*G06K 9/00* (2006.01)
*G06T 11/00* (2006.01)
(Continued)

(52) U.S. Cl.
CPC .......... *G06T 11/003* (2013.01); *A61B 6/032* (2013.01); *A61B 6/14* (2013.01); *A61B 6/466* (2013.01); *A61B 6/469* (2013.01); *A61B 6/501* (2013.01); *A61B 6/5205* (2013.01); *A61B 6/5223* (2013.01); *G06T 15/00* (2013.01); *A61B 6/5258* (2013.01); *G06T 2200/04* (2013.01);
(Continued)

(58) Field of Classification Search
None
See application file for complete search history.

(56) References Cited

U.S. PATENT DOCUMENTS 7,835,561 B2 * 11/2010 Meyer .................. G06T 11/005
    356/343
2004/0208276 A1 * 10/2004 Kaufman ............... A61B 6/032
    378/4
(Continued)

FOREIGN PATENT DOCUMENTS

JP  2007-130240 A     5/2007
KR  10-2010-0070822 A  6/2010
KR  10-2013-0138612 A 12/2013

*Primary Examiner* — Shervin Nakhjavan
(74) *Attorney, Agent, or Firm* — IP Legal Services, LLC

(57) ABSTRACT

A medical image reconstruction system and method for correcting a CT image such that the CT image is located at the center of a three-dimensional (3D) space in order to overcome an error that would otherwise be formed due to an inaccurate position of a patient during Obtaining CT images. After the 3D spatial positions of a 3D medical image are corrected using 3D medical image data, a trajectory of a dental arch is detected. A two-dimensional (2D) medical image is created from the 3D medical image through automatic reconstruction on the basis of the detected trajectory of the dental arch.

11 Claims, 11 Drawing Sheets

(51) Int. Cl.
*A61B 6/03* (2006.01)
*A61B 6/14* (2006.01)
*G06T 15/00* (2011.01)
*A61B 6/00* (2006.01)

(52) U.S. Cl.
CPC .... *G06T 2210/41* (2013.01); *G06T 2219/028* (2013.01); *G06T 2219/20* (2013.01); *G06T 2219/2016* (2013.01)

(56) References Cited

U.S. PATENT DOCUMENTS

| | | | |
|---|---|---|---|
| 2005/0111616 A1* | 5/2005 | Li | A61B 6/025 378/22 |
| 2008/0021502 A1* | 1/2008 | Imielinska | A61B 6/032 607/1 |
| 2008/0232539 A1 | 9/2008 | Pasini et al. | |
| 2010/0053209 A1* | 3/2010 | Rauch | A61B 6/4441 345/619 |
| 2010/0074403 A1* | 3/2010 | Inglese | A61B 6/14 378/39 |
| 2012/0039435 A1* | 2/2012 | Arai | A61B 6/06 378/11 |
| 2013/0022251 A1 | 1/2013 | Chen et al. | |
| 2013/0022252 A1 | 1/2013 | Chen et al. | |
| 2013/0022254 A1 | 1/2013 | Chen | |
| 2013/0022255 A1 | 1/2013 | Chen et al. | |
| 2013/0071001 A1* | 3/2013 | Waechter-Stehle | A61B 6/12 382/132 |
| 2013/0218530 A1* | 8/2013 | Deichmann | A61C 13/0004 703/1 |
| 2013/0235036 A1 | 9/2013 | Fukui | |
| 2013/0266123 A1* | 10/2013 | Yoshida | A61B 6/545 378/98.5 |
| 2013/0308846 A1 | 11/2013 | Chen et al. | |
| 2013/0331697 A1 | 12/2013 | Park et al. | |
| 2014/0099012 A1* | 4/2014 | Begin | G06T 5/006 382/131 |
| 2014/0342301 A1* | 11/2014 | Fleer | A61C 5/025 433/27 |
| 2015/0036790 A1 | 2/2015 | Zoccatelli | |
| 2015/0320380 A1* | 11/2015 | Iijima | A61B 6/4441 378/19 |
| 2015/0335299 A1 | 11/2015 | Chen et al. | |
| 2015/0348229 A1* | 12/2015 | Aguirre-Valencia | G06T 3/20 345/419 |
| 2016/0080719 A1* | 3/2016 | Tsukagoshi | H04N 13/0011 348/46 |

* cited by examiner

Min Cut    Dental Arch    Max Cut
           Coordinate

APPARATUS AND METHOD FOR RECONSTRUCTING MEDICAL IMAGE

CROSS REFERENCE TO RELATED APPLICATION

The present application claims priority to Korean Patent Application No. 10-2015-0037639, filed on Mar. 18, 2015, No. 10-2015-0037652, filed on Mar. 18, 2015, and No. 10-2015-0037657, filed on Mar. 18, 2015, the entire contents of which is incorporated herein for all purposes by this reference.

BACKGROUND

The present invention generally relates to a medical image reconstruction system and method. More particularly, the present invention relates to a medical image reconstruction system and method for correcting the three-dimensional (3D) spatial position of a 3D image.

In general, 3D medical images, such as computed tomography (CT) images or ultrasonic images, provide an advantage in that it is possible to collectively and comprehensively examine a subject using 3D medical images. However, in order to more specifically observe the inner cross-sections of the subject, the use of 2D medical images may be more effective than the use of 3D medical images. When 3D medical images and 2D medical images are displayed together, a user can observe the subject both collectively and precisely.

As an example of a related-art approach of displaying 3D medical images and 2D medical images, Korean Patent Application Publication No. 10-2013-0138612 (published on Dec. 19, 2013) will be described as follows:

A related-art device for displaying 3D medical images and 2D medical images includes: a 3D image acquisition unit for acquiring a 3D medical image of a subject; a cross-section selection unit for selecting at least one cross-section of the subject on the basis of an external input to the acquired 3D medical image; a 2D image acquisition unit for acquiring a 2D medical image by scanning the subject to be corresponding to the selected at least one cross-section; and a display unit for displaying the 2D medical image and the 3D medical image.

Here, the cross-section selection unit includes: a window creator creating at least one window to be positioned above the acquired 3D medical image; a window controller moving the at least one window above the 3D medical image; and an additional cross-section selector additionally selecting at least one cross-section adjacent to the selected at least one cross-section.

In addition, the 2D image acquisition unit includes: a first image acquisition unit acquiring at least one first 2D medical image by scanning the subject to be corresponding to the selected at least one cross-section; a second image acquisition unit acquiring at least one second 2D medical image by scanning the subject to be corresponding to at least one cross-section adjacent to the selected at least one cross-section; and a synthesized image acquisition unit acquiring at least one synthesized 2D medical image by synthesizing the at least one first 2D medical image and the at least one second 2D medical image.

The related-art approach can acquire at least one synthesized 2D medical image by acquiring and synthesizing the 2D medical images corresponding to the selected at least one cross-section and the at least one cross-section adjacent to the selected cross-section. However, this approach cannot acquire a 2D medical image (i.e. a panoramic image or a cephalometric image in the case of a 2D dental image) by reconstructing image information in a specific area of paths along which X-rays are emitted (hereinafter, referred to as X-ray emission paths) from the sagittal or coronal cross-section.

Since 2D medical images corresponding to different cross-sections, which are spaced apart at least predetermined distances, are magnified at different degrees due to the fact that ultrasonic beams or X-ray beams tend to propagate radially, when a 2D medical image is acquired by overlapping medical images in a selection area (range) using a simple image synthesizing method used in the related art, the acquired 2D medical image becomes inaccurate.

When a CT operator is not experienced, the CT operator frequently takes CT images without accurately aligning with the position of a patient (subject). When CT images are taken with the position of the patient being misaligned, it is impossible to prevent horizontal asymmetry or distortion in the facial skeleton, unless CT geometry correction is performed. Thus, when a CT image acquired from a patient without inaccurately aligning the position of the patient is displayed through a medical diagnostic 3D viewer, the initial CT image appears distorted. In addition, when features are extracted from CT volume data or a panoramic image or a cephalometric image is automatically reconstructed without executing a CT geometry correction algorithm, the performance of a reconstruction algorithm is lowered, which is problematic.

In the related art of a dental computed tomography, a panoramic image is reconstructed manually. A user manually inputs the trajectory of the dental arch in a cross-sectional image -of the axial direction. And the panoramic image is generated by reconstructing a certain range of images vertical to the trajectory of the dental arch which is manually input. The reconstructed panoramic image is created by applying the manually input trajectory of the dental arch in a specific cross-section to the entirety of the cross-sections. However, since the positions of the trajectory of the dental arch on the cross-sections are different, when the panoramic image is reconstructed manually, no teeth appear on the panoramic image if the teeth are present outside of the trajectory of the dental arch.

SUMMARY

Accordingly, the present invention is intended to provide a medical image reconstruction system and method which can correct a CT image such that the CT image is located at the center of a three-dimensional (3D) space in order to overcome an error that would otherwise be formed due to an inaccurate position of a patient during obtaining CT images.

Also provided is a medical image reconstruction system and method for correcting an error formed due to an inaccurate position of a patient during obtaining CT images by locating a 3D medical image at the center of the 3D space using previously obtained 3D medical image data and then generating a 2D medical image through automatic reconstruction without additionally obtaining a 2D dental image, for example, a panoramic image or a cephalometric image.

The objects of the present invention are not limited to the above-mentioned objects, and other objects and advantages of the present invention that have not been mentioned will be understood from the following description and will be apparent from the following embodiments of the present invention. In addition, it will be apparent that the objects and advantages of the present invention will be realized by components defined in the appended claims and combination thereof.

According to an aspect of the present invention, a medical image reconstruction system extracts angles of correction according to cross-sectional directions in order to correct the position of a 3D medical image and rotates the 3D medical image using the angles of correction according to cross-sectional directions, thereby performing geometry correction.

As described above, the present invention can correct a CT image such that the CT image is located at the center of a three-dimensional (3D) space in order to overcome an error that would otherwise be formed due to an inaccurate position of a patient during obtaining CT images. It is thereby possible to improve accuracy in the position of each cross-sectional image, whereby more accurate medical diagnosis is enabled.

In addition, the present invention can apply CT geometry correction when automatically generating a panoramic image or a cephalometric image through automatic reconstruction using CT volume data, thereby preventing distortion in the facial skeleton, improving accuracy in the position of each cross-sectional image, and improving the degree of magnification.

Furthermore, the present invention can correct an error formed due to an inaccurate position of a patient during obtaining CT images by locating a 3D medical image at the center of the 3D space using previously-taken 3D medical image data, detect the trajectory of the dental arch, and generate a panoramic image through automatic reconstruction, on the basis of the detected trajectory of the dental arch, without having to additionally take a panoramic image or take any additional images. It is therefore possible to remove additional exposure to X-rays, thereby reducing the level by which a subject (patient) is exposed to X-rays.

In addition, the present invention can remove the necessity of an arm to obtain a predetermined degree of magnification in order to realize a panoramic imaging system or a cephalometric imaging system. It is therefore possible to reduce the medical system as well as a space in which the medical system is disposed.

DETAILED DESCRIPTION OF EMBODIMENTS

The present invention provides an image reconstruction system and method for correcting three-dimensional (3D) spatial positions of a 3D medical image using 3D medical image data and then generating a two-dimensional (2D) medical image, or in the case of a medical image, a cephalometric image through automatic reconstruction.

According to exemplary embodiments of the present invention, an example of 3D medical image data may be computed tomography (CT) volume data, and an example of a 3D medical image may be a CT image. An example of a 2D medical image will be described as being a panoramic image or a cephalometric image. It should be understood, however, the present invention is not limited thereto.

The foregoing object, characteristics, and advantages will be more clearly understood from the following detailed description when taken in conjunction with the accompanying drawings, so that a person skilled in the art to which the present invention relates could easily put the technical idea of the present invention into practice. In the following description of the present invention, detailed descriptions of known functions and components incorporated herein will be omitted in the case that the subject matter of the present invention may be rendered unclear thereby.

Herein, it will be understood that when an element is referred to as being "connected to" another element, not only can it be "directly connected to" the other element, but it can also be "electrically connected to" the other element via an intervening element. It will be further understood that a part "comprising" or "including" a component means that the part may further comprise or include the other components but does not preclude the presence or addition of one or more other components unless clearly indicated otherwise. In addition, singular forms "a", "an", and "the" are intended to include the plural forms as well, unless the context clearly indicates otherwise.

Reference will now be made in greater detail to exemplary embodiments of the present invention with reference to the accompanying drawings.

A medical image reconstruction system according to exemplary embodiments of the present invention is implemented as a computer including a system memory, processing units (a central processing unit (CPU) and a graphic processing unit (GPU)), a graphic card memory, and a memory device. Here, the computer operates on an operating system (OS), such as Windows (Windows XP or a higher version), Linux, Mac OS X, or the like. Through embodiments of the present invention, the computer is referred to an image management system (IMS) or an IMS client. The IMS is connected to an imaging system, such as an X-ray imaging system, and may control the imaging system to execute an image-taking function (an imaging function) or may be provided with image data from the imaging system.

Figure 1:
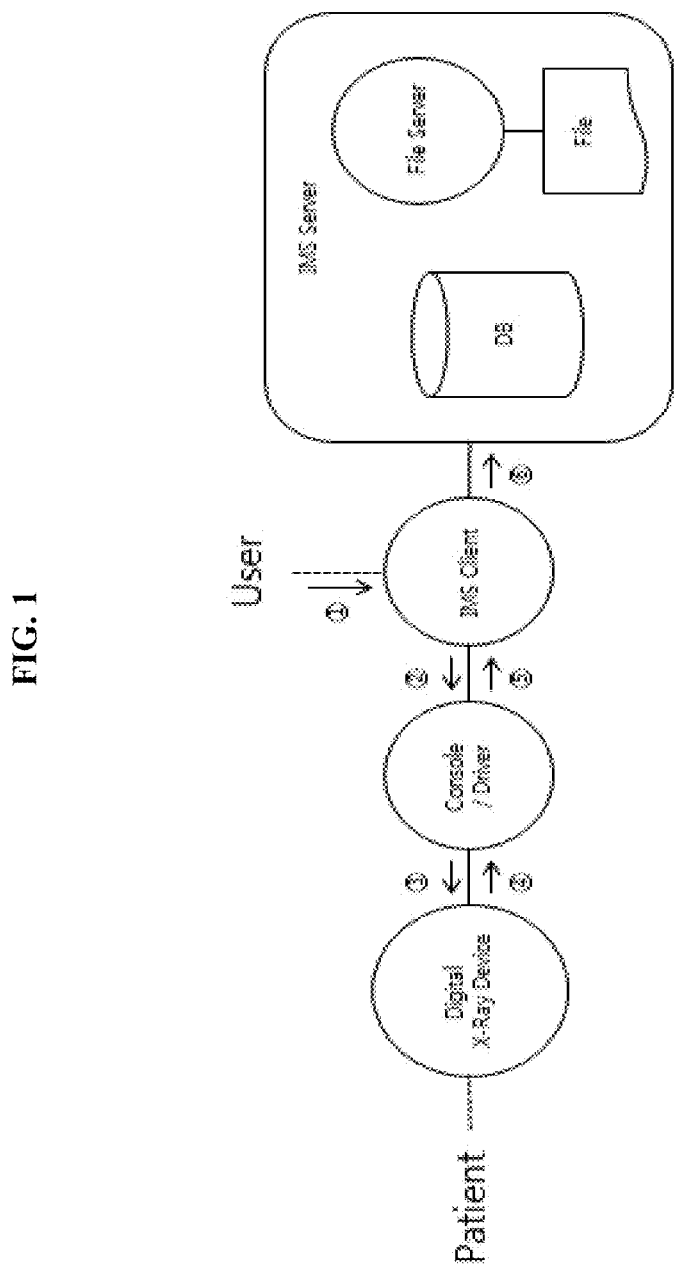
FIG. 1 is a schematic view illustrating a medical image reconstruction system according to an exemplary embodiment of the present invention together with related devices.

FIG. 1 is a schematic view illustrating connection relationships of an IMS client acting as a medical image reconstruction system according to an exemplary embodiment of the present invention and related devices. When a user performs an image-taking function through the IMS client, the IMS client requests a console to take an image. Herein, the console collectively indicates hardware and software for controlling the imaging system. The imaging system acquires image data by taking an image under the control of the console. The image data is transferred to the IMS client through the console and then is transferred by the IMS client to an IMS server, in which the image data is stored. In the IMS client, an executable file for image reconstructing is installed such that the image data is reconstructed by the executable file. In addition, In the IMS client, an execution file for displaying a three-dimensional (3D) images and a two-dimensional (2D) image is installed such that the images may be displayed on a display device connected to the IMS client.

The following embodiments describe respective steps in which an image data reconstruction program (i.e. execution file) allows the IMS client (more specifically, the CPU and/or GPU) to act as an image reconstruction device. The steps may be coded with a variety of computer languages that can be executed by the processing units.

First Embodiment

The first embodiment of the present invention describes a geometry correction system and method as an exemplary medical image reconstruction system and method for correcting the 3D spatial position of a 3D medical image using 3D medical image data acquired by a computed tomography (CT) system. According to the present embodiment, CT geometry correction is applied to CT volume data such that the center of a CT image is located at the center of a display area of a display device. Here, according to the present embodiment, CT geometry correction is performed by setting a reference point using singular point information in the CT volume data and automatically calculating the center. In the case of dental CT volume data, singular point information may be information about the position of the chin line, the arrangement of teeth, the positions of earplugs, the positions of temporomandibular joints (TMJs), the positions of eyes, and the like.

The geometry correction system for medical images according to the present embodiment stores therein volume data transferred from a medical image data providing system. The medical image data providing system may be an X-ray imaging system, an ultrasonic imaging system, a magnetic resonance imaging (MRI) system, a variety of computer-readable storage media, or at least one computer-readable data storage server connected through networks. In the example illustrated in FIG. 1, a digital X-ray system or an IMS server acts as the medical image data providing system.

In the present embodiment, an example of volume data may be CT volume data provided in real time or stored in a storage medium. When the medical image reconstruction system receives CT volume data obtained by taking images of the head of a subject using a CT system (not shown), the medical image reconstruction system extracts the angles of correction of respective cross-sections for multi-planar reconstruction (MPR), i.e. the angles of correction in coronal, sagittal, and axial directions, in order to correct the positions of CT volume data. The angles of correction are extracted according to the cross-sections in order to extract the angles of correction according to the cross-sections. Here, MPR indicates the reconstruction of a plurality of 2D cross-sectional images (X and Y) from 3D cross-sectional images (X, Y, and Z). The coronal, sagittal, and axial directions relate to the cross-sections of the X, Y, and Z axes of 3D volume images.

Angles of correction are extracted for the purpose of geometry correction. Geometry correction is performed by rotating a CT volume image based on angles of rotation (angles of correction) extracted according to the cross-sections. Here, the angles of rotation (angles of correction) may be calculated as three parameters according to the coronal, sagittal, and axial directions.

In the step of extracting angles of correction, reference point information is extracted from CT volume data, and count maps are extracted according to preset angles of rotation using the extracted reference point information. The process of extracting the rotation angle-specific count maps includes a process of extracting angles of rotation for extracting the angle of rotation of a minimum count map from among the rotation angle-specific count maps.

Extraction of reference point information, extraction of count maps, and extractions of angles of rotation will be described in more detail as follows.

First, extractable reference information is extracted from CT volume data. Reference information may be at least one of information about the chin line, information about the arrangement of teeth, reference information using position information of earplugs, position information of TMJs, and position information of eyes. For example, extracting coordinates of the mandibular end (3D coordinates) using reference point information, an overlapping image is acquired by overlapping axial cross-sectional images in a predetermined range of CT volume data. Following threshold values may be used in order to extract only mandibular information when acquiring the overlapping image. Here, an overlapping image-creating formula $g(x, y)$ is represented in Formula 1:

$$g(x, y) = \sum_{z=zs}^{ze} \sum_{y=0}^{h-1} \sum_{x=0}^{w-1} f(x, y, z) \tag{1}$$

In Formula 1, x, y, and z indicate the positional values of the x, y, and z axes of a CT volume image, w indicates a transverse size of a cross-sectional image, and h indicates a vertical size of the cross-sectional image. In addition, zs is a start point on the Z axis, set for image overlapping, and ze is an end point on the Z axis, set for image overlapping. Values of the overlapping start and end points of the CT volume image may vary depending on the characteristics of patients, and empirically-obtained values may be used through optimization. An example thereof is represented in Formula 2:

$$zs = z - 20$$
$$ze = zs - (z*0.45) \quad (2)$$

In addition, an overlapping image-creating condition formula f(x, y, z) is represented in Formula 3:

$$f(x,y,z) = \{g(x,y)+1, t1 < I(x,y,z) < t2\} \quad (3)$$

In Formula 3, I(x, y, z) indicates pixel values of the CT volume image. When designated threshold values are satisfied, the value of the overlapping image g(x, y) is increased. The designated threshold value t1 is 1000, and the designated threshold value t2 is 2000. Here, the designated threshold values t1 and t2 are variable depending on CT systems or image-taking environments, and empirically-obtained values may be used through optimization.

In addition, the central area of the lower jaw is calculated using overlapped image information. Image information of the central area of the lower jaw is extracted from the axial cross-section image in the predetermined range of the CT volume data. Coordinates of a cross-section in which the extracted image information satisfies following conditions are used as the coordinates of the mandibular end. A formula h(x, y) for detecting the coordinates of the mandibular end is represented in Formula 4:

$$h(x, y) = \sum_{z=zs}^{ze} \sum_{y=by-sy}^{by+sy} \sum_{x=bx-sx}^{bx+sx} j(x, y, z) \quad (4)$$

In Formula 4, bx and by are the coordinates of the center of the range designated to detect information of the mandibular end position in the overlapping image, and sx and sy are size values of the area in the relevant range. A formula for setting the relevant range is represented in Formula 5:

$$bx = \frac{1}{2} \left( \sum_{y=0}^{h-1} \sum_{x=0}^{x-1} X(x, y) + \sum_{y=0}^{h-1} \sum_{x=w-1}^{0} X(x, y) \right) \quad (5)$$

$$by = \sum_{y=0}^{h-1} \sum_{x=0}^{w-1} Y(x, y)$$

In addition, a formula X(x, y) and Y(x, y) for detecting coordinates of the center of the X axis in the designated range is represented in Formula 6:

$$X(x,y) = \{x, g(x,y) > t\}$$
$$Y(x,y) = \{y, bx \neq 0\} \quad (6)$$

A threshold value t is set as a reference value in order to set an effective point in the overlapping image. For example, the threshold value t is 40. Here, the threshold value t is variable depending on the characteristics of the image, and an empirically-obtained value may be used through optimization.

For example, both the size values sx and sy of the area for setting the range on the basis of the detected center coordinates are 100. Here, the size values of the area are variable depending on the characteristics of the image, and empirically-obtained values may be used through optimization.

The formula j(x, y, z) for detecting the mandibular end position in the finally set range is represented in Formula 7:

$$j(x,y,z) = \{z, TC = m*m\} \quad (7)$$

In Formula 7, m indicates the size of a mask. When the area of the mask surrounding each pixel within the designated area is searched for, a total number TC in which pixel values satisfy the threshold values t1 and t2 is calculated as in Formula 8:

$$TC = \sum_{my=y-m/2}^{y+m/2} \sum_{mx=x-m/2}^{x+m/2} k(mx, my) \quad (8)$$

$$k(mx, my) = \{TC + 1, t1 < I(x, y, z) < t2\}$$

$$t1 = 1000$$

$$t2 = 2000$$

In Formula 8, when the value of TC is equal to the size of the mask area, the relevant point is used as the coordinates of the mandibular end position.

Rotation angle-specific count maps are extracted using image information about the regions of interest (ROI) on the basis of reference point information. Here, it is set such that the count maps are extracted according to the angles of rotation.

The angle of rotation of the count map having the smallest number of pixels (i.e. the minimum count map) is extracted by measuring the number of effective pixels of the count maps extracted according to the angles of rotation.

The process of extracting the rotation angle-specific count maps according to the present embodiment includes rotating a CT volume image according to preset angles of rotation, extracting image information of the ROI on the basis of reference point information extracted from the rotated CT volume image, and extracting count maps using the image information of the ROI.

The extraction of the ROI will be described in more detail as follows.

Rotation of the CT volume image is repeated at intervals of a preset angle of rotation (e.g. 0.1°) by previously-designated (set) ranges of rotation angle. Here, the intervals of the angle of rotation may be changed to any values other than the interval of 0.1°. The intervals of the angle of rotation to be used may be set depending on the trade-off relationship between processing time and accuracy.

In addition, the rotation of the CT volume image may be performed by reducing the CT volume image in order to improve the processing speed. For example, an original data size of 800×800×600 may be reduced to 400×400×600, 400×400×300, 400×800×300, or so on before being processed. In addition, a preprocessing algorithm, such as noise filtering, may be applied prior to the rotation of the image in order to accurately calculate the angle of rotation for image correction.

For example, according to an embodiment, the ranges of the angle of rotation of the CT volume image designated according to the cross-sections may be set such that the axial direction ranges from −10° to 10°, the sagittal direction ranges from −9° to 9°, and coronal direction ranges from −3° to 3°. The setting of the angles of rotation can be affected by the parameters which can be adjusted for respective systems and is considering the error range of the CT output data.

The rotation of an image repeats the operation of extracting image information and count maps, which will be described later, while changing the angle by rotation angle intervals (e.g. 0.1°) designated in the axial, sagittal, and coronal directions.

The sequence of the rotation of the image may be selected arbitrarily. The angle of rotation may be obtained by obtaining count maps for all directions, or may be obtained by determining the axial direction, followed by determining the sagittal direction and then the coronal direction.

In the rotated CT volume image, image information of the ROI designated for each cross-section is extracted on the basis of information about the mandibular end position (reference point information). Here, the ROI may be set to a size able to include both the upper jaw and the lower jaw. Here, since the setting of the ROI is a factor that may have an effect on the performance of the system (or algorithm) according to the present embodiment, a variety of shapes other than the shape including both the upper jaw and the lower jaw may be set.

The count maps are extracted on the basis of threshold values designated using image information in the ROI. Here, a count map-creating formula g(x, y) is represented in Formula 9:

$$g(x, y) = \sum_{z=r1}^{r2} \sum_{y=0}^{h-1} \sum_{x=0}^{w-1} f(x, y, z) \qquad (9)$$

Here, r1 and r2 indicate height values of the set ROI.

In addition, a count map-creating condition formula f(x, y, z) is represented in Formula 10:

$$f(x,y,z)=\{1, \; t1<I(x,y,z)<t2\} \qquad (10)$$

Here, the threshold value t1 may be designated as 500, and the threshold value t2 may be designated as 1500. These values may be changed depending on CT systems or image-taking environments.

Figure 2:
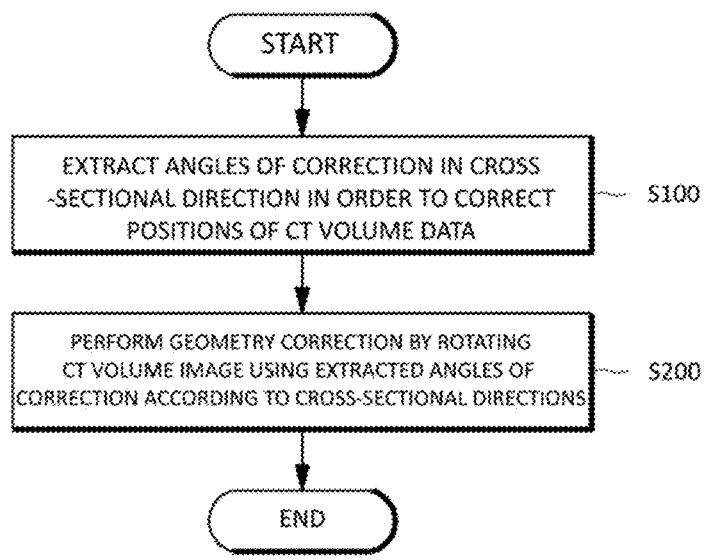
FIG. 2 is a flowchart illustrating a geometry correction method for a medical image according to an embodiment of the present invention.

FIG. 2 is a flowchart illustrating a geometry correction method for a medical image according to the embodiment of the present invention.

When CT volume data is transferred (input), angles of correction of respective cross-sectional directions are extracted for the purpose of position correction of the CT volume data (S100). Here, the process of extracting a correction angle illustrated in FIG. 3 is performed according to cross-sections in order to extract the cross-section-specific angles of correction.

Afterwards, geometry correction is performed by rotating a CT volume image using the angles of correction in cross-sectional directions (S200).

Figure 3:
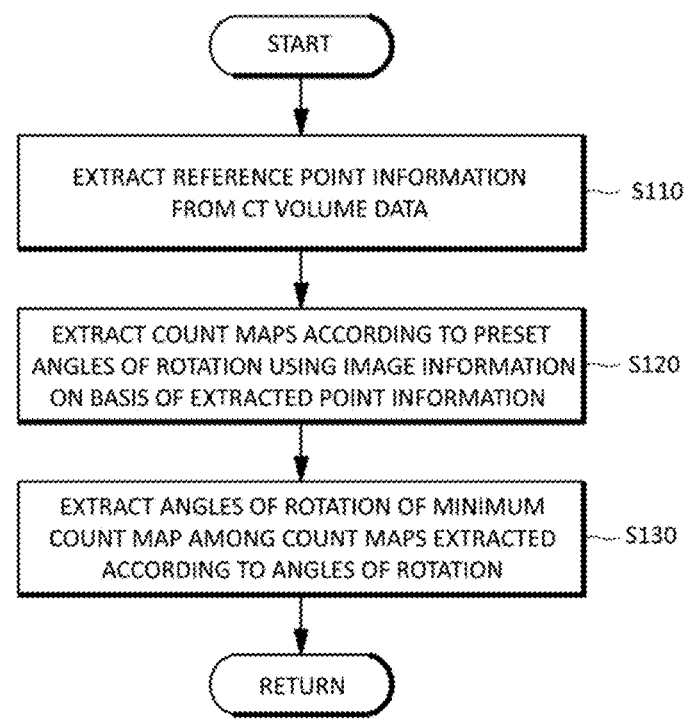
FIG. 3 is a detailed flowchart illustrating the process of extracting a correction angle according to an embodiment of the present invention.

FIG. 3 is a detailed flowchart illustrating the correction angle extraction process S100 according to the embodiment of the present invention.

Reference point information is extracted from CT volume data (S110). Count maps are extracted according to preset angles of rotation using image information according to the extracted reference point information (S120). Here, a subroutine (a process of extracting rotation angle-specific count maps of FIG. 4) is performed for each angle of rotation in order to extract rotation angle-specific count maps.

The angle of rotation of the minimum count map is extracted from among the extracted rotation angle-specific count maps (S130).

Figure 4:
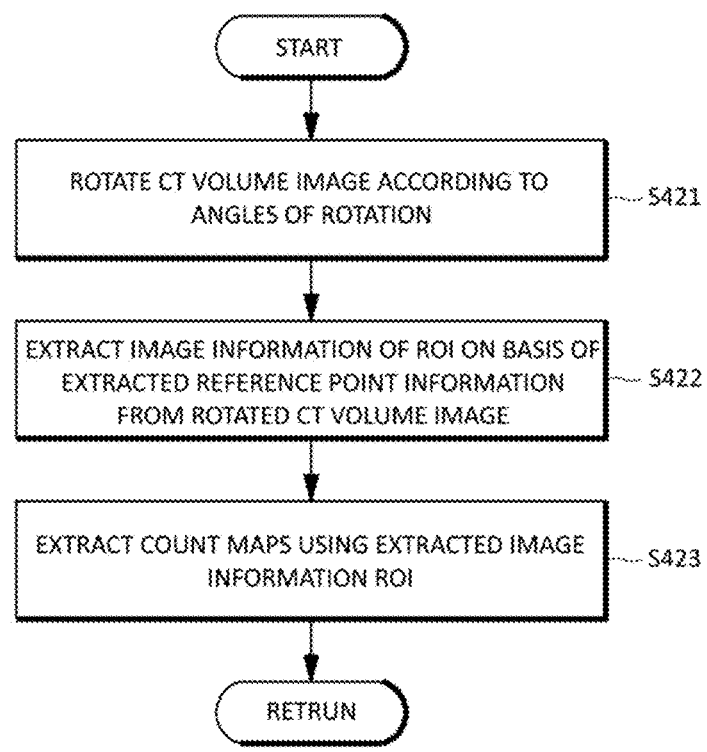
FIG. 4 is a detailed flowchart illustrating the process of extracting rotation angle-specific count maps according to an embodiment of the present invention.

Referring to FIG. 4, the CT volume image is rotated according to the preset angles of rotation (S121). Image information of the ROI is extracted from the rotated CT volume image, on the basis of reference point information (S122). Count maps are extracted using the extracted image information of the ROI (S123).

Second Embodiment

The present embodiment is an image reconstruction system and method for correcting 3D spatial positions of 3D dental image data as an example of 3D medical image data, detecting the trajectory of the dental arch, and then generating a 2D medical image, for example, a panoramic image, through automatic reconstruction from a 3D medical image on the basis of the detected trajectory of the dental arch. The technical idea thereof will be described as follows.

The present embodiment corrects CT volume data by applying CT geometry correction thereto such that a CT image is located at the center of the 3D space and then generates the panoramic image through automatic reconstruction using CT images. Here, in the present embodiment, the panoramic image is generated by reconstructing image information in the intersection area of paths along which X-rays are emitted (hereinafter, referred to as X-ray emission paths), on the basis of the detected trajectory of the dental arch, using characteristic information of teeth on CT images.

That is, according to the present embodiment, first, positional errors are corrected by applying the geometry correction method for medical images as described in the first embodiment, in order to correct errors formed due to the inaccurate position of a patient while CT images are being taken. Here, optimized positions are produced by calculating characteristic values of the ROI designated in CT images. Afterwards, the trajectory of the dental arch is detected by applying a dental arch detection algorithm using the characteristic values of teeth to CT images. Thereafter, an automatic reconstruction algorithm is applied to generate a panoramic image from CT images. Here, the panoramic image is generated by reconstructing image information in the designated area (the intersection area of X-ray emission paths) on the basis of the detected trajectory of the dental arch.

The panoramic image reconstruction system according to the present embodiment reconstructs a panoramic image by applying CT geometry correction to CT volume data such that CT images are located at the center of the 3D space, detecting the trajectory of the dental arch, setting an panoramic image information use area (hereinafter, referred to as a "panoramic image information use area"), and summating image information of geometry-corrected CT images in the set panoramic image information use area on the basis of the detected trajectory of the dental arch.

For geometry correction, at least a portion of the process of correcting the geometry of a medical image described in the first embodiment may be applied.

In order to detect the trajectory of the dental arch, a standard dental arch and coordinate information of a rotation center point (RCP) are set using information about the image-taking sequence of the system, and the trajectory of the dental arch is generated using the set standard dental arch.

The standard dental arch and coordinate information of the RCP are set using information about the image-taking sequence of the imaging system on the basis of position coordinates of the anterior occlusion. For example, a most reasonable position when taking an image using the panoramic imaging system may be set on the basis of position information of the anterior occlusion, or may be set variously in consideration of a position in which a panoramic image is generated.

The standard dental arch and the RCP coordinates set as described above are used when producing X-ray paths. Afterwards, the panoramic image is reconstructed by summating image information of an area designated on the basis of points at which the paths of relevant X-rays intersect the detected trajectory of the dental arch. The X-ray paths for summation are determined depending on the standard dental arch and the positions of the RCP coordinates. The X-ray paths may be produced by calculating paths along which X-rays generated from the position of an X-ray source pass through the positions of the voxels of the CT volume when an image is actually taken using the panoramic imaging system.

For example, the positions of the standard dental arch and the RCP coordinates are set on the Y axis at a distance of 8 mm from the position coordinates of the anterior occlusion in consideration of the voxel size of the CT volume data. The distances by which the positions of the standard dental arch and the RCP coordinates have moved may be applied as values that are produced through empirical optimization. The value 8 mm is an example set in consideration of a position in which the magnification and shrinking of the reconstructed panoramic image can be minimized. Thus, this value is changeable, and may be applied as parameters.

A cubic-spline curve is used in order to generate the trajectory of the dental arch using the preset standard dental arch. In order to generate the trajectory of the dental arch according to the present embodiment, detecting the position coordinates of the anterior occlusion, detecting the coordinates of the fixed dental arch on the basis of the detected position coordinates of the anterior occlusion, detecting the coordinates of the anterior dental arch according to cross-sections on the basis of the detected position coordinates of the anterior occlusion, correcting the coordinates of the dental arch using the detected coordinates of the fixed dental arch and the coordinates of the anterior dental arch, and the trajectory of the dental arch is produced using the coordinates of the dental arch that have been corrected and detected according to the cross-sections.

Figure 5:
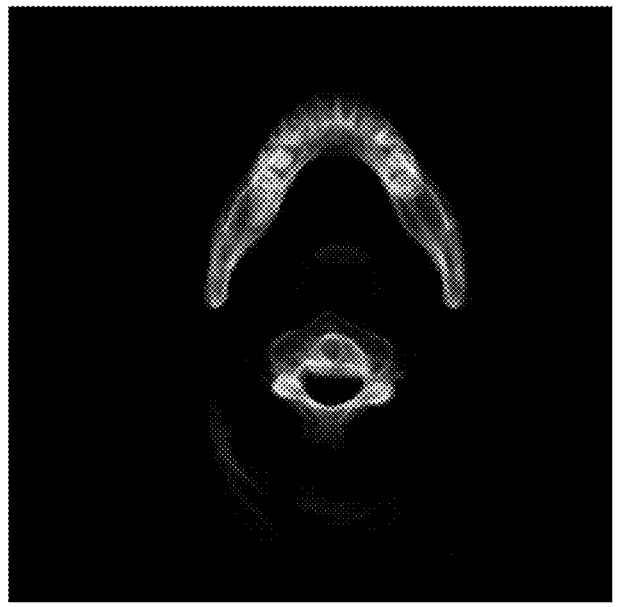
FIG. 5 is a view illustrating the process of extracting an overlapping image of values satisfying threshold values t1 and t2.

In order to detect the position coordinates, an overlapping image satisfying specific threshold values t1 and t2 are extracted from cross-sections, up to a cross-section having a designated height on the basis of the cross-section in the position of the mandibular end (see FIG. 5). For example, the threshold value t1 may be 1000, and threshold value t2 may be 2000. These values may be changed depending on CT systems or image-taking environments. Here, a noise filter may be applied in order to improve accuracy when detecting the position coordinates of the anterior occlusion from the extracted overlapping image.

Figure 6:
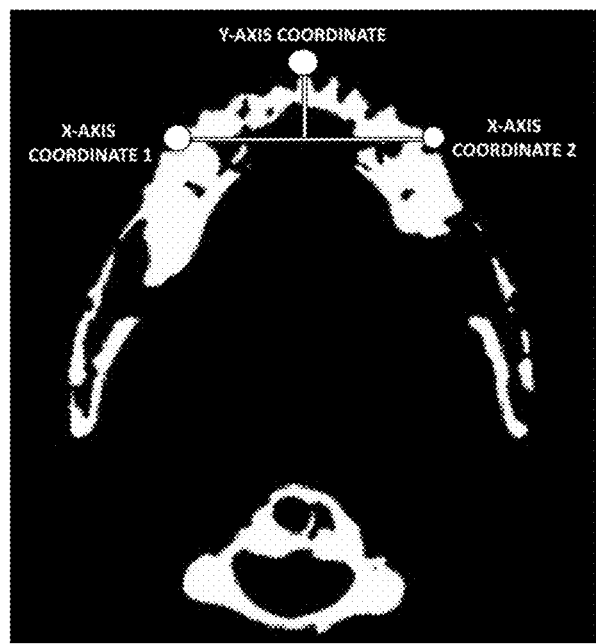
FIG. 6 is a view illustrating the process of detecting position coordinates of the anterior occlusion on X and Y axes.

Referring to FIG. 6, a Y-axis coordinate satisfying a specific threshold value t3 is extracted in order to detect a point having a higher level of overlapping of teeth from the extracted overlapping image. For example, the threshold t3 may be 50, and may be varied depending on CT systems or image-taking environments. The X-axis coordinate is extracted by calculating a median value by extracting the start and end portions on the X axis at a distance ranging from 1 cm to 1.5 cm on the basis of the relevant Y axis. The distance of movement on the Y axis may be applied as a value that is produced through empirical optimization. Since the value ranging from 1 cm to 1.5 cm is an example set in consideration of the shape of the dental arch, this value is changeable and may be applied as a parameter. The Z axis coordinate is arbitrarily designated as a point 3.5 cm above the coordinates of the end position of the chin. Here, the value of 3.5 cm is set reflecting an empirical result. Statistically, the distance from the end of the chin to the occlusion is 2.4 cm for young children and 4.0 cm for adults. Thus, the optimal distance set considering the size or age of the patient is changeable and may be applied as a parameter.

Figure 7:
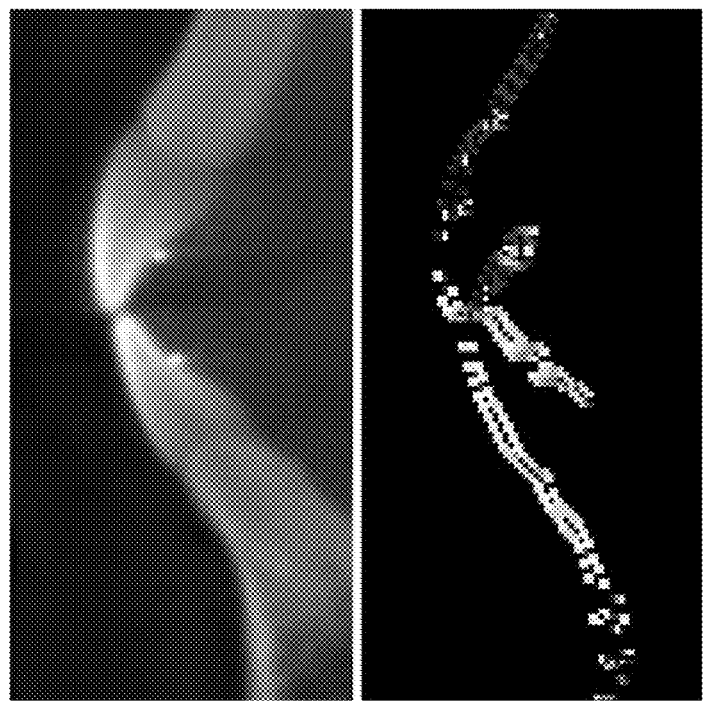
FIG. 7 is a view illustrating an average image and a gradient image of the anterior occlusion.

Referring to FIG. 7, an image is generated using an average value of each pixel in a specific ROI on the basis of the position coordinates of the primarily-extracted anterior occlusion, and a gradient image is extracted from the average image. Here, the ROI indicates a rectangular area that may include the anterior teeth, and values for setting the ROI size may be used as parameters.

Figure 8:
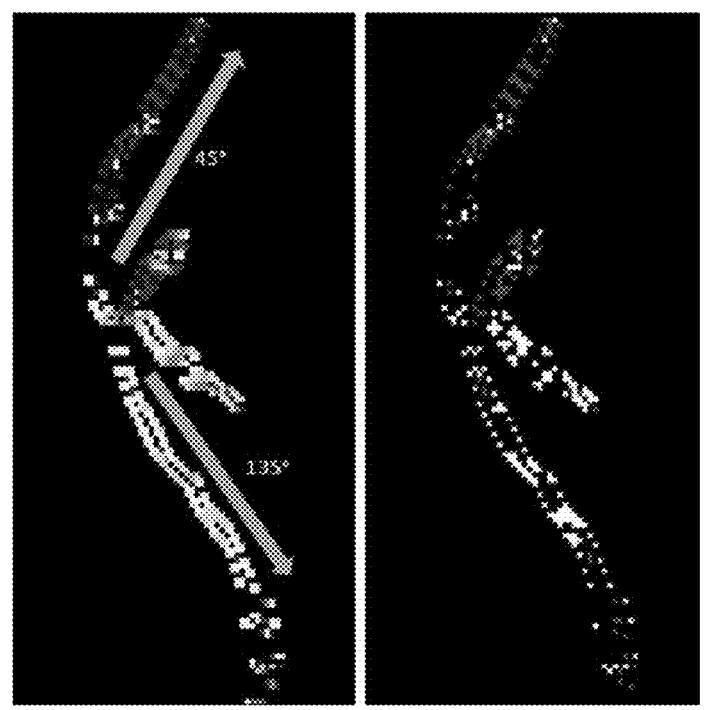
FIG. 8 is a view illustrating an angle extraction image from the gradient image.

As illustrated in FIG. 8, the angles of the teeth in the upper jaw and the lower jaw in the extracted gradient image are calculated. A teeth angle calculation formula A(x, y) is represented in Formula 11:

$$A(x, y) = \sum_{y=0}^{ry} \sum_{x=0}^{ry} \tan^{-1}(G(x, y) \times (180 \div \pi)) \quad (11)$$

In Formula 11, G(x, y) indicates a pixel value of the gradient image.

In order to improve the efficiency of calculation, the angles other than 45° and 135° are set to 0. This is because the distribution of angles, i.e. the angle 45° for the upper jaw and the angle of 135° for the lower jaw, is significantly high. Here, a point at which the difference in the number between the angle 45° and the angle 135° is extracted by examining the number of angles distributed in a specific area of images in which the angles of teeth are calculated to detect the position of the teeth occlusion, and the relevant coordinates are used as position coordinates of the anterior occlusion.

Figure 9:
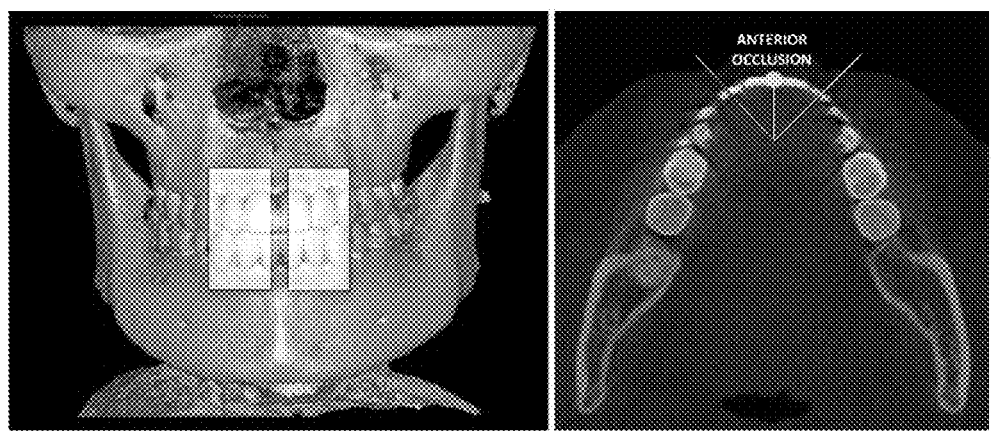
FIG. 9 is a view illustrating a search area for the calculation of coordinates of the fixed dental arch at 45°.

For detecting the coordinates of the fixed dental arch, histograms can be created for search areas (see FIG. 9) which is at left 45° and right 45° of the y axis from the center which is moved from the position coordinates of the anterior occlusion by 1.5 cm along y axis. The histograms may be between the threshold values t1 and t2 of the search areas. The distance of movement on the Y axis may be applied as a value obtained through empirical optimization. Since the value 1.5 cm is an example set in consideration of the shape of the dental arch, this value is changeable and may be applied as a parameter. For example, the threshold value t1 may be 1000, and the threshold value t2 may be 2000. These values may be changed depending on CT systems and image-taking environments.

Figure 10:
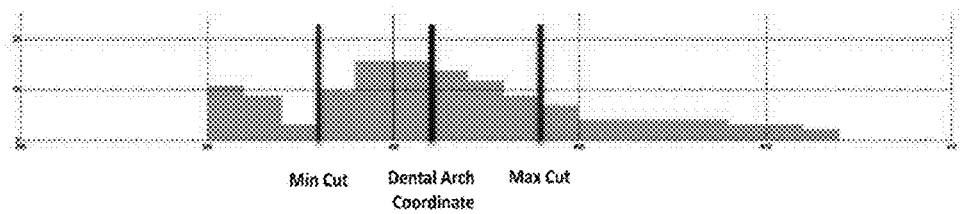
FIG. 10 is a view explaining a method of extracting coordinates of the dental arch using the histographic distribution of the search area.

As illustrated in FIG. 10, after minimum 20% and maximum 20% is cut from a total number in the histogram, the center points are extracted as the coordinates of the dental arch. As described above, after the coordinates of the fixed dental arch at 45° are extracted from the position coordinates of the anterior occlusion, the extracted coordinates are used on all cross-sections.

Figure 11:
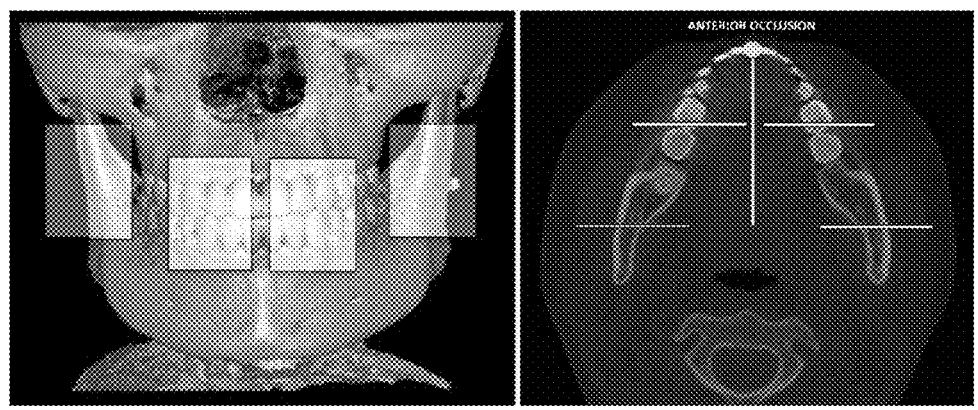
FIG. 11 is a view illustrating a search area for the calculation of coordinates of the fixed dental arch at 90°.

In addition, another histograms can be created for search areas (see FIG. 11) which is at left 90° and right 90° of the y axis from the centers which is moved from the position coordinates of the anterior occlusion by 2.5 cm and 6.5 cm along y axis. The histograms also can be between the threshold values t1 and t2 of the search areas. These distances of movement on the Y axis may be applied as a value produced through empirical optimization. Since the values 2.5 cm and 6.5 cm are examples set in consideration of the shape of the dental arch, these values are changeable and may be applied as parameters. For example, the threshold value t1 is 1000, and the threshold value t2 is 2000. These vales may be changed depending on CT systems and image-taking environments.

Figure 12:
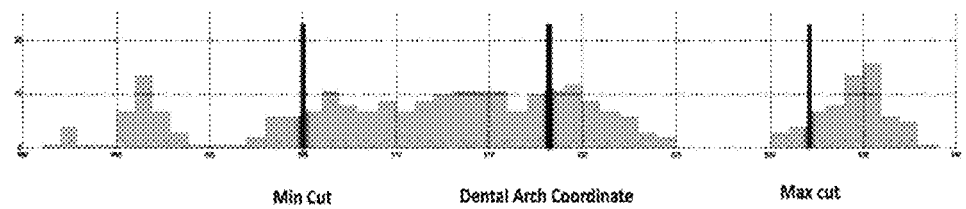
FIG. 12 is a view explaining a method of extracting coordinates of the dental arch using the histographic distribution of the search area.

As illustrated in FIG. 12, after minimum 20% and maximum 20% is cut from a total number in the histogram, the center points are extracted as the coordinates of the dental arch. As described above, after the coordinates of the fixed dental arch at 90° are extracted from the position coordinates of the anterior occlusion, the extracted coordinates are used on all cross-sections.

Figure 13:
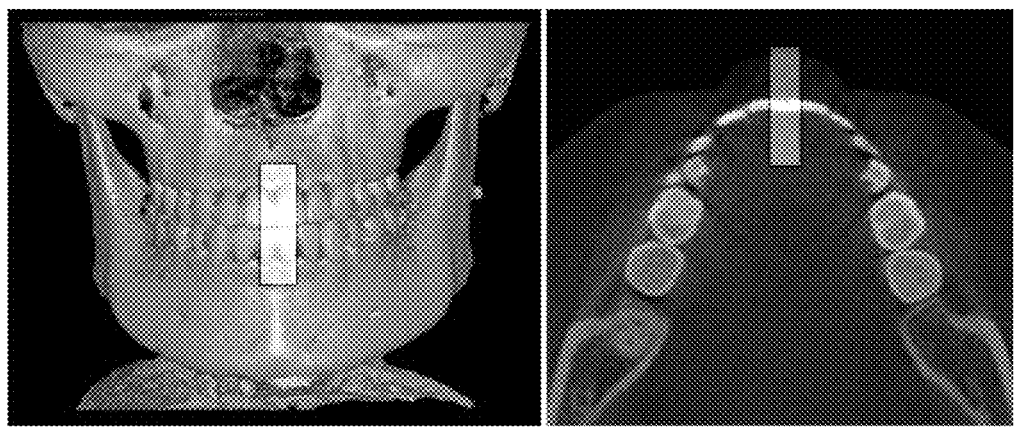
FIG. 13 is a view illustrating a search area for the calculation of coordinates of the anterior dental arch.

In addition, for detecting the coordinates of the anterior dental arch, a histogram can be created for a search area (see FIG. 13) on the basis of the coordinates of the anterior occlusion. The histogram also can be between the threshold values t1 and t2 of the search area. For example, the threshold value t1 is 1000, and the threshold value t2 is 2000. These vales may be changed depending on CT systems and image-taking environments.

Figure 14:
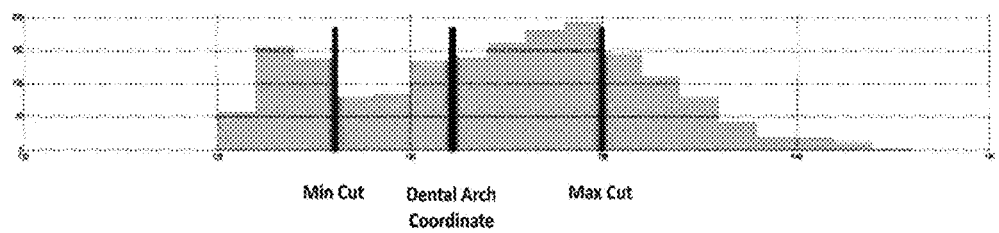
FIG. 14 is a view explaining a method of extracting coordinates of the anterior dental arch using the histographic distribution of the search area.

As illustrated in FIG. 14, minimum 20% and maximum 20% is cut from a total number in the histogram, and the center point is extracted as the coordinates of the dental arch. The process of extracting the coordinates of the anterior dental arch as described above is repeatedly performed according to the cross-sections.

In addition, when the coordinates of the dental arch are corrected, the curve of the trajectory of the dental arch may be deformed if the coordinates of the dental arch are present above the coordinates of the anterior dental arch along the Y axis. In order to prevent this problem, the coordinates of the dental arch are corrected such that the coordinates of the fixed dental arch are positioned 1 mm below the coordinates of the anterior dental arch. In this case, the distance of correction may be applied as a value produced through empirical optimization. Since the value 1 mm is an example set in consideration of the shape of the dental arch, this value is changeable and may be applied as a parameter.

The process of correcting the coordinates of the dental arch as described above is repeatedly performed according to the cross-sections. In addition, in order to produce the trajectory of the dental arch using the coordinates of the dental arch detected through cross-section-specific correction as described above, the process of producing the trajectory of the dental arch uses a cubic-spline curve represented in Formula 12:

$$B(t)=P_0(1-t)^3+3P_1t(1-t)^2+3P_2(1-t)+P_3t^3, t\in[0,1] \quad (12)$$

In addition, the trajectory of the dental arch produced using the cubic-spline curve is divided into equal distances according to the voxel size of the CT volume or is divided using the information of the image-taking sequence of the system. Here, the trajectory of the dental arch is divided while moving to the right and left with respect to the center point thereof.

In order to set a panoramic image information use area, intersectional points of the trajectory of the standard dental arch and the previously obtained trajectory of the dental arch are calculated and then coordinates of the orthogonal intersection area which has a designated distance from the standard dental arch. Here, the coordinates of the relevant orthogonal intersection area are perpendicular to the gradient of the standard dental arch and the RCP coordinates. In addition, since the anterior teeth and the posterior teeth differ in the thickness and reference area, different summation areas (image information use area) may be applied. The summation areas of the anterior teeth and the posterior teeth are set using previously-designated values considering the relevant characteristics.

The panoramic image is reconstructed by creating a weight map, adjusting the ratio of image information reflected on the panoramic image that is reconstructed, and summating "image information in the panoramic image information use areas" according to weights in the weight map.

After the reconstruction of the panoramic image, the size of the reconstructed panoramic image may be adjusted.

In addition, the reconstructed panoramic image may be subjected to additional image processing.

When the panoramic image is reconstructed using the trajectory of the dental arch detected from the CT volume, a 3D gradient map of the CT volume is produced in order to improve the characteristics and clearness of the teeth, and is used as weights during summation. Here, the 3D gradient map is extracted according to the cross-sections (axial, sagittal, and coronal cross-sections) using a Sobel mask represented in Formula 13, in which gradient information of the sagittal and coronal cross-sections is synthesized using information about path-specific angles in consideration of the characteristics of X-ray paths.

$$\begin{array}{ccc} \text{Sobel Mask} & \text{Row} & \text{Column} \\ & -1\ -2\ -1 & -1\ 0\ 1 \\ & 0\ \ 0\ \ 0 & -2\ 0\ 2 \\ & 1\ \ 2\ \ 1 & -1\ 0\ 1 \end{array} \quad (13)$$

$$G_{val} = G_{coronal} * (1.0 - W_{angle}) + G_{Sagittal} * W_{angle}$$

In addition, the panoramic image is adjusted by creating an opacity table. That is, in consideration of the characteristics of the CT number, the opacity table is created by applying a gamma curve to an area that does not exceed a specific threshold value. The opacity table is a type of lookup table, and is used as a means for adjusting the ratio of image information reflected on the reconstructed panoramic image. An opacity table creating formula T(x) is represented in Formula 14:

$$T(x) = \sum_{x=0}^{s} f(x) \quad (14)$$

$$f(x) = \begin{cases} (x/(t-1))^g \times x, & x < t \\ x, & x \geq t \end{cases}$$

In Formula 14, s indicates the size of the opacity table, and g indicates gamma curve power. A threshold value t is an applicable value produced through empirical optimization. When the threshold value t is 2000, this value is an example set in consideration of the CT number.

In addition, in the reconstruction of the panoramic image, "image information in the panoramic image information use area" from the image information of the CT image of which the geometry is corrected, is summated according to the weights of the weight maps. Here, points at which the orthogonal intersection area of the standard dental arch intersects the detected coordinates of the dental arch are produced, and image information of the designated area is summated on the basis of the points.

Furthermore, in the summation, after values in the panoramic image information use area are applied to the opacity table, the weights are applied. Here, the weights may be applied by combining Gaussian weights and gradient weights or by applying Gaussian weights and gradient weights independently. In addition, the weights may be implemented as intensity values of pixels in the area of the summation.

Here, when the gradient weights are used, information about the relevant area is acquired from the 3D gradient maps using information about the position coordinates of the summation area. Information about the relevant area uses interpolation results to which bi-linear interpolation is applied. Since gradient information values are characterized by having large values around edges, the gradient information values are smoothed by applying a Gaussian mask in order to use information about the interior and surroundings of the edges. Result information is converted into gradient weights through normalization. The gradient weights are added to the Gaussian weights in order to create final weights. In addition, summation is performed by applying the finally-created weights to result values that have passed through the opacity table.

The panoramic image is reconstructed by applying above-described processing to the entirety of X-ray path areas of the trajectory of the dental arch detected according to the cross-sections.

In addition, the size of the reconstructed panoramic image on the CT volume data is adjusted. That is, the size of the image is adjusted by cutting specific areas in order to draw a result image similar to the image taken by the panoramic imaging system or to remove unnecessary peripheral portions. Here, when it is unnecessary to adjust the size of the image, the process of adjusting the size of the panoramic image may be omitted.

After panoramic image processing, the reconstructed panoramic image is subjected to post processing, thereby improving the quality thereof. In order to maximize an improvement in the quality of the image, pre-processing may be applied before the geometry correction.

Figure 15:
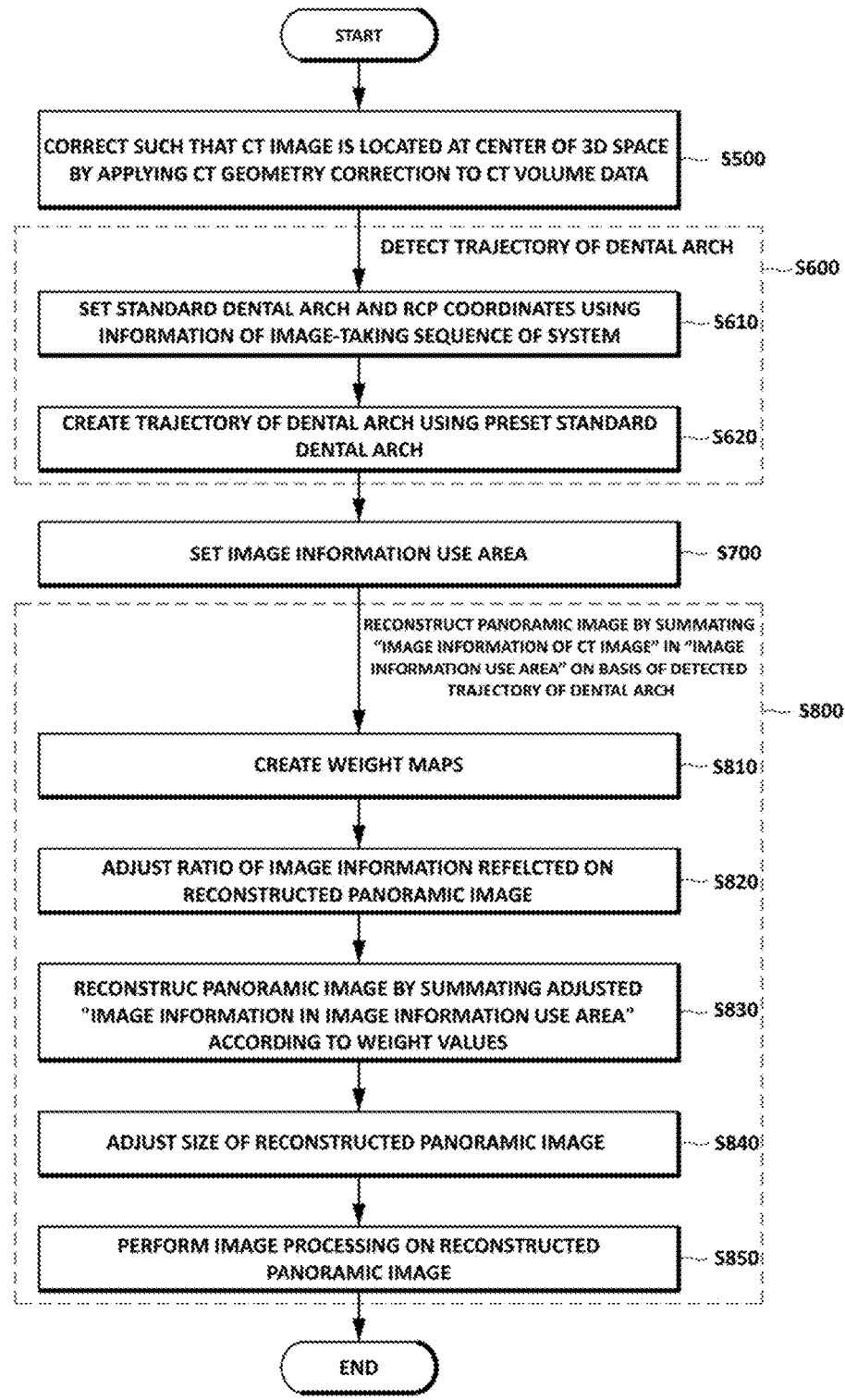
FIG. 15 is a flowchart illustrating a panoramic image reconstruction method as an example of the medical image reconstruction according to an exemplary embodiment of the present invention.

FIG. 15 is a flowchart illustrating a medical image reconstruction method according to an exemplary embodiment of the present invention. Since detailed descriptions thereof have been given above, operations thereof will now be described in brief.

First, CT volume data is corrected such that a CT image is located at the center of the 3D space by applying CT geometry correction to the CT volume data (S500). The geometry correction process has been described in detail in relation to the first embodiment.

Afterwards, the trajectory of a dental arch is detected (S600). Here, the process of detecting the trajectory of a dental arch includes a process of setting a standard dental arch and RCP coordinates using information about the image-taking sequence of the system (S610) and a process of creating the trajectory of a dental arch using the set standard dental arch (S620). The process of creating the trajectory of a dental arch using the set standard dental arch (S620) will be described later with reference to FIG. 16.

Thereafter, a panoramic image information use area is set (S700).

Afterwards, the panoramic image is reconstructed by summating "information about the geometry-corrected CT image" in the "panoramic image information use area" on the basis of the detected trajectory of the dental arch (S800). Here, the process of reconstructing the panoramic image (S800) includes a process of creating weight maps (S810), a process of adjusting the ratio of image information reflected on the panoramic image (S820), and a process of reconstructing the panoramic image by summating the "image information in the adjusted panoramic image information use area" according to the weights of the weight maps (S830). In addition, the process of reconstructing the panoramic image (S800) further includes a process of adjusting the size of the reconstructed panoramic image (S840). Furthermore, the process of reconstructing the panoramic image (S800) further includes a process of performing image processing on the reconstructed panoramic image (S850).

Figure 16:
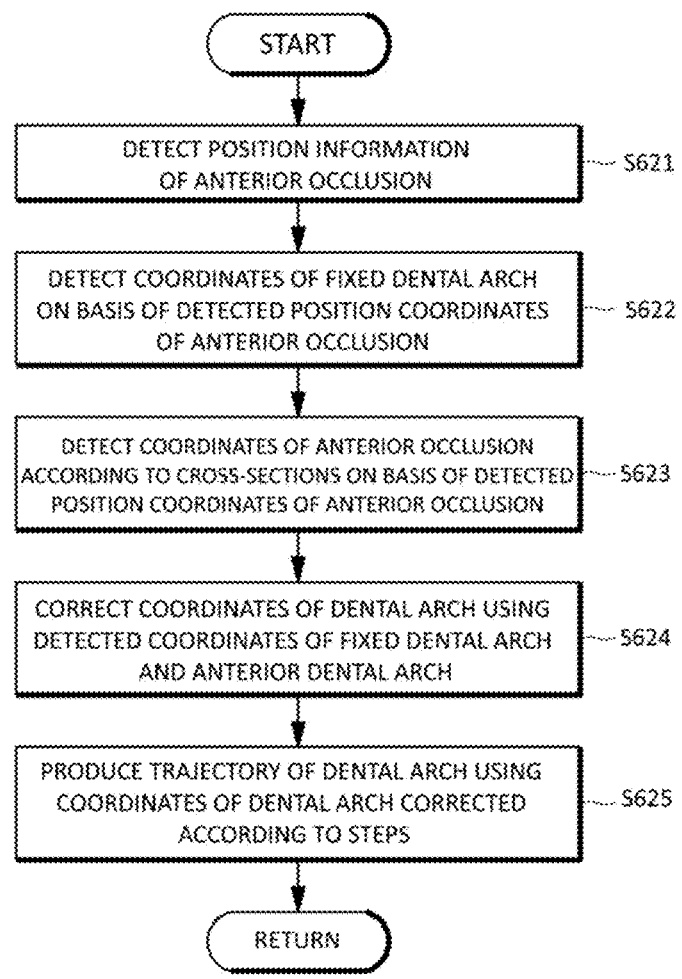
FIG. 16 is a detailed flowchart illustrating the process of creating the trajectory of the dental arch according to an exemplary embodiment of the present invention.

FIG. 16 is a detailed flowchart illustrating the process of creating the trajectory of a dental arch using the set standard dental arch (S620) according to an exemplary embodiment of the present invention.

First, the position coordinates of the anterior occlusion are detected (S621).

The coordinates of the fixed dental arch are detected on the basis of the detected position coordinates of the anterior occlusion (S622). The coordinates of the anterior dental arch according to the cross-sections are detected on the basis of detected position coordinates of the anterior occlusion (S623). The coordinates of the dental arch are corrected using the coordinates of the fixed dental arch and the coordinates of the anterior dental arch (S624). The trajectory of the dental arch is produced using the coordinates of the dental arch that have been corrected according to the cross-sections (S625).

Third Embodiment

The present embodiment is an image reconstruction system and method for correcting 3D spatial positions of a 3D medical image using 3D medical image data and then generating a 2D medical image, for example, a cephalometric image, through automatic reconstruction from the 3D medical image. The technical idea thereof will be described as follows.

The present embodiment corrects CT volume data by applying CT geometry correction thereto such that a CT image is located at the center of the 3D space and then generates a cephalometric image through automatic reconstruction using CT images. In the present embodiment, the cephalometric image is generated by reconstructing image information in a specific area of X-ray emission paths on the sagittal or coronal cross-sections of the CT images.

That is, according to the present embodiment, first, positional errors are corrected by applying the geometry correction method for medical images as described in the first embodiment, in order to correct errors formed due to the inaccurate position of a patient while CT images are being taken. Here, optimized positions are produced by calculating characteristic values of the ROI designated in CT images. Afterwards, an automatic reconstruction algorithm is applied to generate a cephalometric image from CT images. Here, the Cephalometric image is generated by reconstructing image information in the designated area (the specific area of the X-ray emission paths) on the sagittal or coronal cross-sections.

The process of reconstructing a cephalometric image according to the present embodiment reconstructs a cephalometric image by performing geometry correction by applying CT geometry correction to CT volume data such that a CT image is located at the center of the 3D space, setting an image information use area to be used in image reconstruction, and then summating "image information of geometry-corrected CT images" in the set image information use area.

Position coordinates of an X-ray source are set using information about the image-taking sequence of the system, and an image information use area is set based on the set position coordinates. Here, the position coordinates of the X-ray source are set using information about the image-taking sequence of the system on the basis of the position coordinates of the anterior occlusion. For example, in the present embodiment, a most reasonable position when taking an image using the cephalometric imaging system may be set on the basis of position information of the anterior occlusion, or may be set variously in consideration of a position in which a cephalometric image is taken. Since the position coordinates of the X-ray source are set in this manner, the cephalometric image is reconstructed afterwards by summating image information of the area designated on the basis of the position coordinates of the X-ray source. Here, the X-ray paths for summation are determined depending on the position of the X-ray source. The X-ray paths to be used may be produced by calculating paths along which X-rays generated from the position of the X-ray source pass through the positions of the voxels of the CT volume when an image is actually taken using the cephalometric imaging system. In addition, at least a portion of overall areas of the CT volume image in the sagittal or coronal cross-sectional direction may be set as summation areas (image information use area).

The cephalometric image is reconstructed by adjusting the ratio of image information reflected on the cephalometric image that is reconstructed and summating "image information in the adjusted image information use areas". The step of adjusting the size of the reconstructed cephalometric image may be further included. In addition, the reconstructed cephalometric image may be subjected to image processing.

Here, cephalometric image is adjusted by creating an opacity table. That is, in consideration of the characteristics of the CT number, the opacity table is created by applying a gamma curve to an area that does not exceed a specific threshold value. The opacity table is a type of lookup table, and is used as a means for adjusting the ratio of image information reflected on the Cephalometric image that is reconstructed according to the present invention. An opacity table creating formula T(x) is represented in Formula 15:

$$T(x) = \sum_{x=0}^{s} f(x) \qquad (15)$$

$$f(x) = \begin{cases} (x/(t-1))^g \times x, & x < t \\ x, & x \geq t \end{cases}$$

In Formula 15, s indicates the size of the opacity table, and g indicates gamma curve power. A threshold value t is an applicable value produced through empirical optimization. When the threshold value t is 2000, this value is an example set in consideration of the CT number.

In addition, in the reconstruction of the cephalometric image, "image information in the cephalometric information use area" from the image information of the CT image of which the geometry is corrected, is summated.

In the summation, values in the cephalometric information use area are applied to the opacity table. In addition, the weights of summation data (image information) may be adjusted using specific information (e.g. edges or gradient). Here, in consideration of the characteristics of X-rays, the weights may be implemented as attenuation factors or may be implemented as intensity values of pixels in the area of the summation. In addition, summation is performed by applying the finally-created weights to result values that have passed through the opacity table.

The cephalometric image is reconstructed by applying above-described processing to the entirety of X-ray path areas. In addition, the size of the reconstructed cephalometric image on the CT volume data is adjusted. That is, the size of the image is adjusted by cutting specific areas in order to draw a result image similar to the image taken by the cephalometric imaging system or to remove unnecessary peripheral portions. Here, when it is unnecessary to adjust the size of the image, the process of adjusting the size of the Cephalometric image may be omitted.

Afterwards, the reconstructed cephalometric image is subjected to post processing, thereby improving the quality thereof. In order to maximize an improvement in the quality of the image, pre-processing may be applied before the geometry correction.

Figure 17:
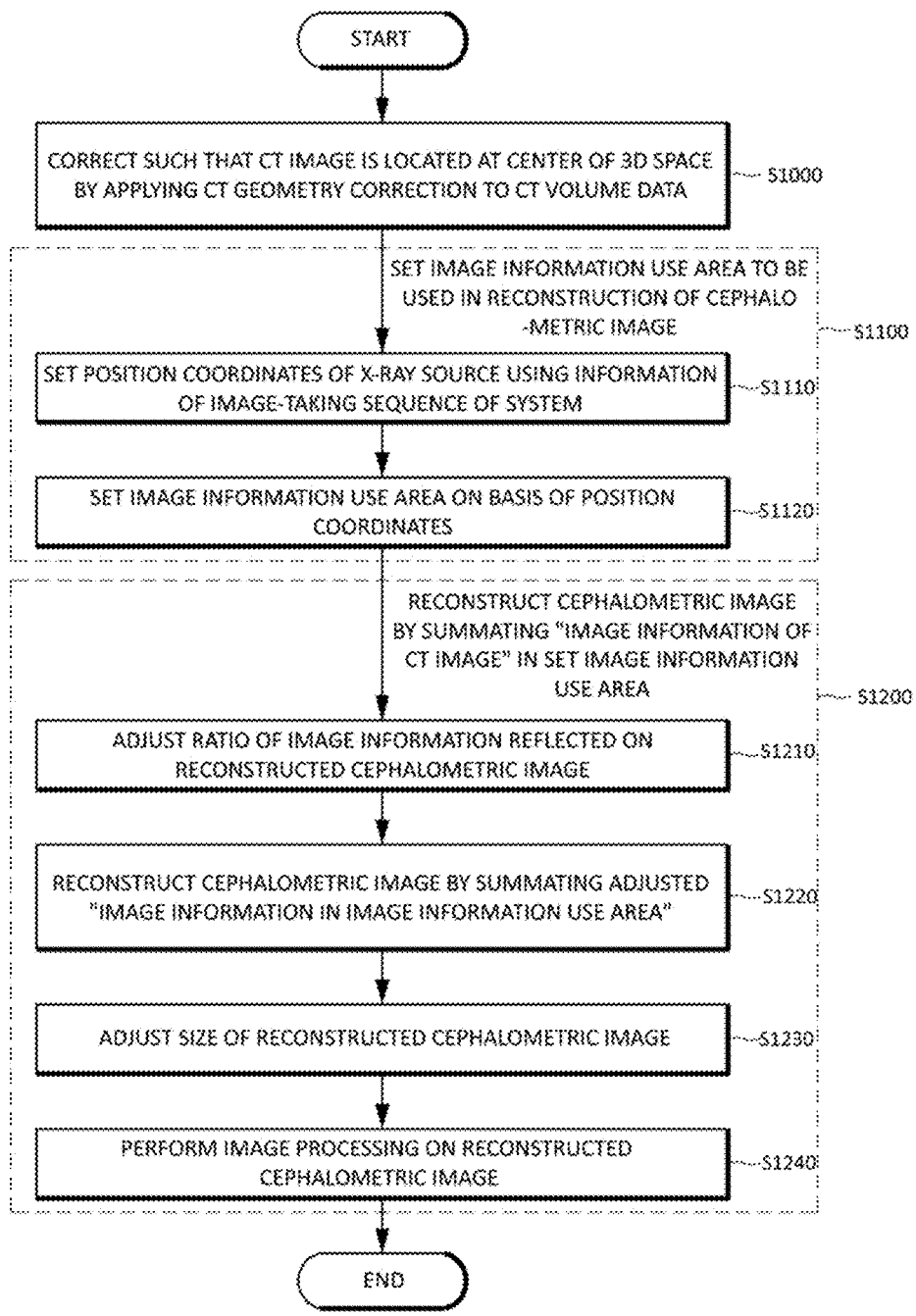
FIG. 17 is a flowchart illustrating a cephalometric image reconstruction method as an example of the medical image reconstruction according to an exemplary embodiment of the present invention.

FIG. 17 is a flowchart illustrating a cephalometric image reconstruction method according to an exemplary embodiment of the present invention. Since detailed descriptions thereof have been given above, operations thereof will now be described in brief.

First, CT volume data is corrected such that a CT image is located at the center of the 3D space by applying CT geometry correction to the CT volume data (S1000). The geometry correction process has been specifically described above in relation to the first embodiment.

Afterwards, an image information use area to be used in the reconstruction of the cephalometric image is set (S1100). This process includes a process of setting the position coordinates of the X-ray source using information about the image-taking sequence of the system (S1110) and a process of setting the image information use area on the basis of the set position coordinates (S1120).

Thereafter, the cephalometric image is reconstructed by summating "image information of the CT image, the geometry of which is corrected", in the set image information use area (S1200). Here, the process of reconstructing the cephalometric image (S1200) includes a process of adjusting the ratio of image information reflected on the cephalometric image that is reconstructed (S1210) and a process of reconstructing the cephalometric image by summating "image information in the adjusted cephalometric image information use area" (S1220). After the process of reconstructing the cephalometric image (S1200), a process of adjusting the size of the reconstructed cephalometric image (S1230) may further be performed. Furthermore, the process of reconstructing the cephalometric image (S1200) further includes a process of performing image processing on the reconstructed cephalometric image (S1240).

The medical image reconstruction method according to the present invention as described above may be embodied as computer readable program instructions stored in a computer readable storage medium, the computer readable program instructions being able to be executed by a variety of computing means. The computer readable storage medium may include one or a combination of program instructions, data files, data structures, and so on. The program instructions stored in the storage medium may be program instructions specially designed and constructed for the present invention or program instructions known and available to a person skilled in the field of software. Examples of the computer readable storage medium include magnetic media, such as a hard disk, a floppy disk, and a magnetic tape; optical media, such as compact disc read only memory (CD-ROM) and a digital versatile disk (DVD); magneto-optical media, such as a floptical disk; and other hardware devices specially designed to store and execute program instructions, such as read only memory (ROM), random access memory (RAM), and flash memory. In addition, the storage medium may be in the form of light or a carrier wave that conveys signals specifying program instructions, data structures, or the like, or a transmission medium, such as a metal wire or a waveguide, through which the signals are transmitted. Examples of the program instructions include not only machine language codes generated by compilers, but also advanced language codes that may be executed by a computer using an interpreter. The hardware devices described above may be constructed such that they can operate as one or more software modules for performing the operations of the present invention, and vice versa.

Although the exemplary embodiments of the present invention have been described in relation to the specific embodiments and in conjunction with the accompanying drawings, the present invention is by no means limited thereto. A person skilled in the art will appreciate that various substitutions, modifications, and changes are possible, without departing from the scope and spirit of the present invention as disclosed in the accompanying claims. Therefore, the scope of the present invention is not limited to the foregoing embodiments but shall be defined by the appended claims and equivalents thereof.

What is claimed is:

1. A medical image reconstruction system comprising:
an image management system configured to be connected to an X-ray imaging system and a console for controlling the X-ray imaging system, transferring and processing an image data from the X-ray imaging system, and the image management system including a memory configured to store the image data and a processor configured to perform at least one operation of reconstructing image data,
wherein the processor is configured to extract angles of correction according to cross-sectional directions to correct a position of a three-dimensional medical image and perform geometry correction by rotating the three-dimensional medical image using the angles of correction according to cross-sectional directions, and
wherein the processor is configured to extract a reference point information from the three-dimensional medical image, extract count maps according to preset angles of rotation using image information on basis of the reference point information, and extract an angle of rotation of a minimum count map of the count maps extracted according to the angles of rotation.

2. The medical image reconstruction system according to claim 1, wherein
the three-dimensional medical image data is medical image data produced by obtaining a computed tomography (CT) image of a head of a subject, and
the reference point information is one of information about a chin line, information about an arrangement of teeth, reference information using an object, position information of a temporomandibular joint (TMJ), and position information of eyes in the three-dimensional medical image.

3. The medical image reconstruction system according to claim 1, wherein the processor is configured to rotate the three-dimensional medical image according to preset angles of rotation, extract image information of a region of interest on basis of the reference information from the rotated three-dimensional medical image, and extract the count maps using the image information of the region of interest.

4. The medical image reconstruction system according to claim 1, wherein the processor is configured to extract the angles of rotation of the minimum count map by measuring a number of effective pixels of the count maps extracted according to the angles of rotation and extracting a count map having a smallest number of pixels.

5. The medical image reconstruction system according to claim 1, wherein the processor is configured to detect a trajectory of a dental arch in the three-dimensional medical image, set an image information use area in which a panoramic image information use area including the trajectory of the dental arch is set, and reconstruct a panoramic image by summating image information of the three-dimensional medical image in the panoramic image information use area on basis of the trajectory of the dental arch.

6. The medical image reconstruction system according to claim 1, wherein the processor is configured to set a cephalometric image information use area to be used in reconstruction of a cephalometric medical image in the three-dimensional medical image and reconstruct the cephalometric medical image by summating image information of the three-dimensional medical image in the cephalometric image information use area.

7. The medical image reconstruction system according to claim 6, wherein the processor is configured to set position coordinates of an X-ray source using information about an image-taking sequence and set the cephalometric image information use area by summating image information of the three-dimensional medical image in the cephalometric image information use area on basis of the position coordinates of the X-ray source.

8. A medical image reconstruction system comprising:
an image management system configured to be connected to an X-ray imaging system and a console for controlling the X-ray imaging system, transferring and processing an image data from the X-ray imaging system, and the image management system including a memory configured to store the image data and a processor configured to perform at least one operation of reconstructing the image data,
wherein the processor is configured to set a standard dental arch and coordinates of a rotation center point using information about an image-taking sequence and detect a trajectory of a dental arch using the standard dental arch, and
wherein the processor is configured to detect position coordinates of an anterior occlusion in the three-dimensional medical image, detect coordinates of a fixed dental arch on basis of the position coordinates of the anterior occlusion, detect coordinates of an anterior dental arch according to cross-sections, correct coordinates of the dental arch using the coordinates of the fixed dental arch and the coordinates of the anterior dental arch, and create the trajectory of the dental arch by calculating the trajectory of the dental arch using the corrected coordinates of the dental arch.

9. A medical image reconstruction method comprising:
extracting angles of correction according to cross-sectional directions for position correction of three-dimensional medical image data; and
performing geometry correction by rotating a three-dimensional medical image using the angles of correction according to the cross-sectional directions,
wherein the medical image reconstruction method comprises:
extracting a reference point information from the three-dimensional medical image;
extracting count maps according to preset angles of rotation using image information on basis of the reference point information; and extracting an angle of rotation of a minimum count map of the count maps extracted according to the angles of rotation.

10. The medical image reconstruction method according to claim 9, further comprising:
setting an image information use area to be used in reconstruction of a two-dimensional medical image; and
reconstructing the two-dimensional medical image by summating the three-dimensional medical image data in the image information use area.

11. The medical image reconstruction method according to claim 10, wherein the two-dimensional medical image comprises a panoramic image or a cephalometric image.

\* \* \* \* \*